US00PP13227P2

(12) United States Plant Patent
Hofmann

(10) Patent No.: US PP13,227 P2
(45) Date of Patent: Nov. 12, 2002

(54) NEW GUINEA IMPATIENS PLANT NAMED 'FISNICS SCARLET BLUSH'

(76) Inventor: Birgit Hofmann, Gassenweg 29, 56170 Bendorf (DE)

( * ) Notice: Subject to any disclaimer, the term of this patent is extended or adjusted under 35 U.S.C. 154(b) by 22 days.

(21) Appl. No.: 09/921,481

(22) Filed: Aug. 6, 2001

(51) Int. Cl.[7] ..... A01H 5/00
(52) U.S. Cl. ..... Plt./318

(58) Field of Search ..... Plt./318

*Primary Examiner*—Kent L. Bell
(74) *Attorney, Agent, or Firm*—C. A. Whealy

(57) ABSTRACT

A new and distinct cultivar of New Guinea Impatiens plant named 'Fisnics Scarlet Blush', characterized by its outwardly spreading, rounded and uniformly mounded plant habit; freely branching and freely flowering habit; large rounded bright scarlet red-colored flowers with a purple-colored eye that are positioned above and beyond the foliage; and dark green-colored leaves.

1 Drawing Sheet

BOTANICAL CLASSIFICATION/CULTIVAR DESIGNATION

*Impatiens hawkeri* cultivar 'Fisnics Scarlet Blush'.

BACKGROUND OF THE INVENTION

The present Invention relates to a new and distinct cultivar of New Guinea Impatiens plant, botanically known as *Impatiens hawkeri*, and hereinafter referred to by the name 'Fisnics Scarlet Blush'.

The new Impatiens is a product of a planned breeding program conducted by the Inventor in Hillscheid, Germany. The objective of the breeding program is to develop new compact Impatiens cultivars that flower relatively early and have large rounded flowers with attractive flower color.

The new Impatiens originated from a cross made by the Inventor in May, 1997 of the *Impatiens hawkeri* cultivar 'Moala', disclosed in U.S. Plant Pat. No. 10,301, as the female, or seed parent, with the *Impatiens hawkeri* cultivar 'Antigua', disclosed in U.S. Plant Pat. No. 8,283, as the male, or pollen parent. The cultivar 'Fisnics Scarlet Blush' was discovered and selected by the Inventor as a flowering plant within the progeny of the stated cross in a controlled environment in Moncarapacho, Portugal in March, 1998.

Asexual reproduction of the new cultivar by terminal cuttings taken in Moncarapacho, Portugal, since March, 1998, has shown that the unique features of this new Impatiens are stable and reproduced true to type in successive generations.

SUMMARY OF THE INVENTION

The following traits have been repeatedly observed and are determined to be the unique characteristics of 'Fisnics Scarlet Blush'. These characteristics in combination distinguish 'Fisnics Scarlet Blush' as a new and distinct Impatiens cultivar:

1. Outwardly spreading, rounded and uniformly mounded plant habit.
2. Freely branching and freely flowering habit.
3. Large rounded bright scarlet red-colored flowers with a purple-colored eye that are positioned above and beyond the foliage.
4. Dark green-colored leaves.

Plants of the new Impatiens can be compared to plants of the female parent, the cultivar 'Moala'. In side-by-side comparisons conducted by the Inventor in Hillscheid, Germany, plants of the new Impatiens differed from plants of the cultivar 'Moala' in the following characteristics:

1. Plants of the new Impatiens have darker green leaves than plants of the cultivar 'Moala'.
2. Plants of the new Impatiens have lighter red-colored flowers than plants of the cultivar 'Moala'.

Plants of the new Impatiens can be compared to plants of the male parent, the cultivar 'Antigua'. In side-by-side comparisons conducted by the Inventor in Hillscheid, Germany, plants of the new Impatiens differed from plants of the cultivar 'Antigua' in the following characteristics:

1. Plants of the new Impatiens have darker green leaves than plants of the cultivar 'Antigua'.
2. Plants of the new Impatiens have darker red-colored flowers than plants of the cultivar 'Antigua'.

Plants of the new Impatiens are similar to plants of the cultivar 'Tarawa', disclosed in U.S. Plant Pat. No. 10,320, in flower color. However, in side-by-side comparisons conducted by the Inventor in Hillscheid, Germany, plants of the new Impatiens differed from plants of the cultivar 'Tarawa' in the following characteristics:

1. Plants of the new Impatiens are shorter, broader and have shorter internodes than plants of the cultivar 'Tarawa'.
2. Plants of the new Impatiens have darker green-colored leaves than plants of the cultivar 'Tarawa'.
3. Stem color of plants of the new Impatiens is brown red whereas stem color of plants of the cultivar 'Tarawa' is red purple.
4. Flowers of plants of the new Impatiens are flat whereas flowers of plants of the cultivar 'Tarawa' are somewhat cupped.

Plants of the new Impatiens are also similar to plants of the cultivar 'Marpesia', disclosed in U.S. Plant Pat. No. 8,401, in flower color. However, in side-by-side comparisons conducted by the Inventor in Hillscheid, Germany, plants of the new Impatiens differed from plants of the cultivar 'Marpesia' in the following characteristics:

1. Plants of the new Impatiens are more compact than plants of the cultivar 'Marpesia'.

2. Plants of the new Impatiens have narrower leaves than plants of the cultivar 'Marpesia'.
3. Plants of the new Impatiens have slightly darker red-colored flowers than plants of the cultivar 'Marpesia'.
4. Flowers of plants of the new Impatiens are flat whereas flowers of plants of the cultivar 'Marpesia' are cupped.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens.

The photograph comprises a side perspective view of a typical flowering plant of 'Fisnics Scarlet Blush' grown in a 12-cm container about 10 to 11 weeks after planting a young rooted plant.

DETAILED BOTANICAL DESCRIPTION

The cultivar 'Fisnics Scarlet Blush' has not been observed under all possible environmental conditions. The phenotype may vary somewhat with variations in environment such as temperature, light intensity, daylength, water status and/or fertility level, without, however, any variance in genotype.

The following observations and measurements describe plants grown in Hillscheid, Germany, under commercial practice in a glass-covered greenhouse. Rooted young plants were planted in 12-cm containers in late February and the following observations and measurements were taken about 10 to 11 weeks later. During the production of the plants, day temperatures ranged from 18 to 24° C. and night temperatures were about 18° C. In the following description, color references are made to The Royal Horticultural Society Colour Chart except where general terms of ordinary dictionary significance are used.

Commercial classification: New Guinea Impatiens cultivar 'Fisnics Scarlet Blush'.

Parentage:

*Female parent.*—*Impatiens hawkeri* cultivar 'Moala', disclosed in U.S. Plant Pat. No. 10,301.

*Male parent.*—*Impatiens hawkeri* cultivar 'Antigua', disclosed in U.S. Plant Pat. No. 8,283.

Propagation:

*Type cutting.*—Terminal tip cuttings.

*Time to initiate roots.*—Summer: About 8 to 9 days at 24° C. Winter: About 10 days at 21° C.

*Time to produce a rooted cutting.*—Summer: About 15 days at 24° C. Winter: About 18 days at 21° C.

*Root description.*—Numerous, fibrous, and freely branching; 158D to 179D in color.

Plant description:

*General appearance.*—Outwardly spreading, low, rounded and uniformly mounded plant growth habit; dense and bushy; freely branching and flowering habit.

*Crop time.*—From a rooted cutting, about 9 to 10 weeks are required to produce finished flowering plants in 12-cm containers.

*Plant height.*—About 10.5 cm.

*Plant diameter or spread.*—About 35.5 cm.

*Lateral branches.*—Quantity per plant: About 10 to 12. Length: About 9 cm. Diameter: About 7 mm. Internode length: About 4 cm. Color: 181A.

*Foliage description.*—Arrangement: Primarily in whorls. Length: About 11.2 cm. Width: About 3.7 cm. Shape: Elliptic. Apex: Acuminate. Base: Acute. Margin: Serrulate with ciliation. Texture: Smooth, occasionally weakly rugose, glabrous. Color: Young foliage, upper surface: 137A. Young foliage, lower surface: 185A. Mature foliage, upper surface: 137A to 139A. Mature foliage, lower surface: 185B. Venation, upper surface: 53B to 53C. Venation, lower surface: 53A to 53B. Petiole: Length: About 3.25 cm. Diameter: About 2.5 mm. Color: 53B to 53C.

Flower description:

*Flower type and flowering habit.*—Single and large rounded bright scarlet red-colored flowers with a purple-colored eye. Freely and continuously flowering; usually about 8 to 10 flowers and flower buds per lateral branch. Flowers positioned above and beyond the foliage and typically face upward or outward. Petals self-cleaning; gynoecium persistent. Flowers not fragrant.

*Flower longevity.*—Flowers last about 7 to 10 days on the plant.

*Flowering season.*—Year-round under greenhouse conditions; in the garden, flowering from spring until fall. Plants begin flowering about 9 weeks after planting.

*Flower buds.*—Length: About 2.3 cm. Diameter: About 1.7 cm. Shape: Ovoid. Color: 42A.

*Flower length.*—About 7.1 cm.

*Flower width.*—About 6.9 cm.

*Flower depth.*—About 5 mm.

*Petals.*—Quantity: Five per flower, imbricate. Length: Banner petal: About 2.6 cm. Lateral and base petals: About 3 cm. Width: Banner petal: About 5 cm. Lateral and base petals: About 3.4 cm. Shape: Roughly cordate. Apex: Emarginate, lobed. Base: Attenuate. Margin: Entire. Aspect: Mostly flat. Texture: Smooth; velvety. Color: When opening, upper surface: 43A. When opening, lower surface: 42A. Fully opened, upper surface: 43A to 43B; color does not fade with subsequent development; eye zone, 74B to 74C. Fully opened, lower surface: 43B.

*Spur.*—Quantity: One per flower. Length: About 6.1 cm. Diameter: At apex: About 0.5 mm. At flower: About 2.25 mm. Aspect: Curved downward. Color: 53D.

*Peduncles.*—Length: About 5.8 cm. Diameter: About 2 mm. Strength: Strong, flexible. Color: Between 47A and 53A.

*Reproductive organs.*—Androecium: Stamen number: Five fused at anthers, hooded; filaments free. Anther length: About 6.5 mm. Anther shape: Obovate. Anther color: 43A. Pollen amount: Moderate. Pollen color: 8D. Gynoecium: Pistil quantity: One per flower. Pistil length: About 6 mm. Stigma color: 60D. Ovary: Five-celled. Ovary color: 187A.

*Seeds.*—Seed development has not been observed.

Disease/pest resistance: Plants of the new Impatiens have not been observed to be resistant to pathogens and pests common to Impatiens.

It is claimed:

1. A new and distinct cultivar of New Guinea Impatiens plant named 'Fisnics Scarlet Blush', as illustrated and described.

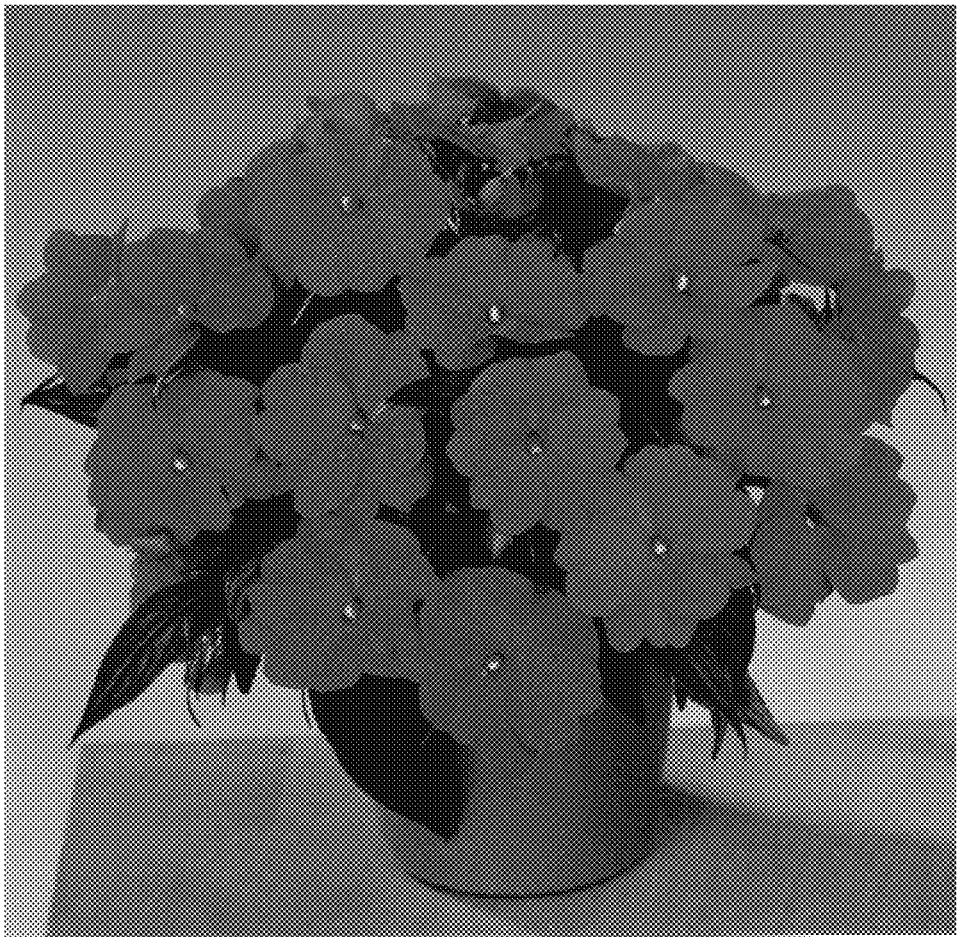

* * * * *